United States Patent [19]

Krapcho et al.

[11] Patent Number: 4,894,451

[45] Date of Patent: Jan. 16, 1990

[54] UNSYMMETRICAL 1,4-BIS(AMINOALKYLAMINO)-ANTHRACENE-9,10-DIONES AND DERIVATIVES

[75] Inventors: A. Paul Krapcho, South Burlington; Miles P. Hacker, Williston, both of Vt.; John J. Landi, Jr., Cresco, Pa.; J. J. McCormack, Burlington, Vt.; Kenneth J. Shaw, Orangeburg, N.Y.

[73] Assignee: The University of Vermont, Burlington, Vt.

[21] Appl. No.: 222,360

[22] Filed: Jul. 19, 1988

Related U.S. Application Data

[63] Continuation of Ser. No. 718,103, Apr. 1, 1985, abandoned.

[51] Int. Cl.⁴ .................. C07C 87/64; C07D 295/12
[52] U.S. Cl. .................. 544/156; 546/204; 548/528; 552/255; 514/908
[58] Field of Search .................. 544/156; 546/204; 548/528; 260/377

[56] References Cited

U.S. PATENT DOCUMENTS

| | | | |
|---|---|---|---|
| 3,446,817 | 5/1969 | Harvey et al. | 260/377 |
| 3,576,587 | 4/1971 | Kalopissis et al. | 260/377 |
| 4,456,552 | 6/1984 | Murdock et al. | 260/377 |

OTHER PUBLICATIONS

Krapcho et al, *J. Org. Chem.*, vol. 49 (12-1984) pp. 5253-5255.

*Primary Examiner*—Robert W. Ramsuer
*Attorney, Agent, or Firm*—Foley & Lardner, Schwartz, Jeffery, Schwaab, Mack, Blumenthal & Evans

[57] ABSTRACT

The disclosure describes unsymmetrical 1,4-bis-(aminoalkylamino)-anthracene-9,10-diones useful in the treatment of neoplasms. Also described is a process of preparing same starting from 1,4-dimethoxyanthracene-9,10-dione which is reacted with an aminoalkylamine. The reaction product is treated with a dialkylaminoethylamine or a N-heteroethylamine to give the unsymmetrical compound.

11 Claims, No Drawings

UNSYMMETRICAL 1,4-BIS(AMINOALKYLAMINO)-ANTHRACENE-9,10-DIONES AND DERIVATIVES

This application is a continuation of application Ser. No. 718,103, filed Apr. 1, 1985, now abandoned.

BACKGROUND OF INVENTION (a) Field of the Invention

This invention relates to unsymmetrical 1,4-bis-(aminoalkylamino)-anthracene-9,10-diones and derivatives thereof. The invention also relates to a process of preparing these compounds as well as to the treatment of human neoplasms in an animal bearing host.

(b) Description of Prior Art

The recent literature discloses a variety of symmetrically substituted 1,4-bis-(aminoalkylamino)-anthracene-9,10-diones which are useful in the treatment of human neoplasms. For example, U.S. Pat. No. 4,197,249 issued Apr. 8, 1980, discloses such symmetrically substituted 1,4-bis-(aminoalkylamino)-anthrcene-9,10-diones. Other references to symmetrical compounds include:

R. K.-Y. Zee-Cheng, G. Podrebarac, C. S. Menon and C. C. Cheng. *J. Med. Chem.* 22, 501 (1979).
C. C. Cheng, G. Zbinden, and R. K.-Y. Zee-Cheng. *J. Pharm. Sci.* 68, 393 (1979).
R. K.-Y Zee-Cheng and C. C. Cheng. *J. Med. Chem.* 21, 291 (1978).
K. C. Murdock, R. G. Child, P. F. Fabio, and R. B. Angier, *J. Med. Chem.* 22, 1024 (1979).
K. K. Johnson et al, *Cancer Treat. Repts.* 63, 425 (1979).
R. E. Wallace, K. C. Murdock, R. B. Angier, F. E. Durr. *Cancer Res.* 39, 1570 (1979).
R. K.-Y. Zee-Cheng and C. C. Cheng. *Drugs of the Future* 8, 229 (1983).

To our knowledge, however, there is no prior art in the scientific literature for unsymmetrically substituted 1,4-bisaminoalkylamino-anthracene-9,10-diones and for the synthesis of these compounds.

SUMMARY OF THE INVENTION

It is the primary object of the invention to provide new unsymmetrically 1,4-substituted anthracene-9,10-diones which are useful for treating human neoplasms in an animal bearing host.

It is a further object of the present invention to provide a process for the synthesis of new unsymmetrically 1,4-substituted anthracene-9,10-diones possessing the above-mentioned properties.

It is still a further object of the present invention to provide a substance having lower toxicity and fewer side effects than any 1,4-bis-(aminoalkylamino)-anthracene-9,10-diones symmetrically substituted compounds used heretofore for the treatment of neoplasms.

It is yet a further object of the present invention to provide novel unsymmetrically substituted 1,4-bis-(aminoalkylamino)-anthracene-9,10-diones.

The above and other objects are achieved in accordance with the present invention by providing compounds of formula (I) and salts of such compounds:

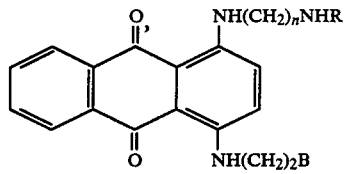

wherein:

B represents lower dialkyl amino groups having 1 to 4 carbon atoms, such as dimethylamino and diethylamino, and cyclic systems such as morpholino, pyrrolidino, and piperidino;

n represents 3, 4 or 5.

R represents hydrogen, alkanoyl, such as acetyl or propionyl, benzyloxycarbonyl, and alkylsulfonyl such as methanesulfonyl. Preferably, R represents hydrogen.

Unsymmetrically substituted compounds of the general formula (I) demonstrate efficacy as antineoplastic agents. Suitable salts of these compounds, such as the hydrohalides, for example the hydrochloride, acetates, sulfates, phosphates, nitrates, tartrates, citrates, maleates, succinates, fumarates, methane sulfonates and oxalates also show activities comparable to the free bases.

Among the compounds which have demonstrated the most significant biological activity are those in which R is hydrogen, B is a dimethylamino group and n=3 and 4. Thus, 1-(4-aminobutylamino)-4-(2-dimethylaminoethylamino)-anthracene-9,10-dione (in which in formula I R=H, B=N(CH$_3$)$_2$ and n=4) has manifested notable antineoplastic activity in studies in vitro (L-1210 lymphoid leukemia) and in vivo.

The testing procedures utilized are described in the Journal of Medicinal Chemistry, 25, 952 (1982).

The compounds according to the present invention may be prepared by reacting 1,4-dimethoxyanthracene-9,10-dione of the formula

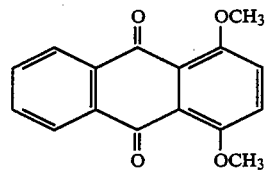

in solution, preferably methylene chloride, as solvent, with an aminoalkylamine of the formula

in which n and R are the same as defined above, in the presence of light, such as irradiation from a sunlamp, to give a compound of formula

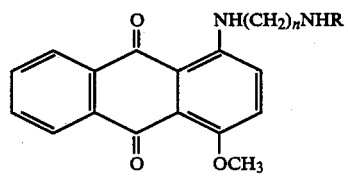

The compound of formula II can be prepared by the method described by A. Paul Krapcho et al in *J. Org. Chem.* Vol. 49, 1984, p. 5254.

The next step includes heating the compound of formula (IV) with an amine selected from the group consisting of a dialkylaminoethylamine and a N-heteroethylamine, which will give a compound of formula (I).

For example, the compounds can generally be prepared by a two-step photolytic-thermolytic procedure as outlined below:

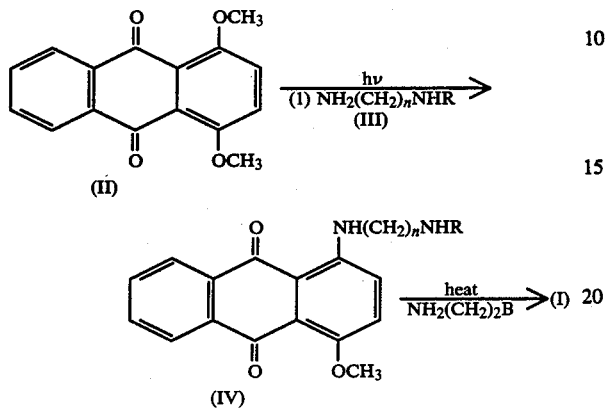

In the above formulae, n, R and B are as defined above. The appropriate substituted aminoalkylamine III is added to a methylene chloride solution of 1,4-dimethoxyanthracene-9,10-dione (II), there being a 2-5 molar excess of the former. The solution is irradiated, the solvent is removed and the product purified by column chromatography on silica gel and recrystallized from a suitable solvent to yield a compound of formula (IV). In certain cases purification may be facilitated by acetylation of the crude photolysate with acetic anhydride to yield the corresponding amides. Thermolysis of compound (IV) in the presence of N,N-dimethylethylenediamine followed by chromatography produces compound I, where $B=N(CH_3)_2$.

The therapeutic composition including compounds of formula (I) and the novel compounds (I) of the present invention inhibit transplanted mouse tumor growth and induce regression and/or palliation of leukemia and related cancers in mammals when administered in amounts ranging from about 5 mg to 200 mg per kilogram of body weight per day. A preferred dosage regimen for optimal results depends on the specific compound. The dosage regimen may be adjusted to bring about the optimum therapeutic response. The active compounds may be administered by the oral, intravenous, intermuscular, or subcutaneous routes.

EXAMPLES

This invention will be described in greater detail in conjunction with the following specific examples which are given only as an illustration of the invention and in no way are intended to limit the scope of the present invention.

EXAMPLE I 1-(3-aminopropylamino)-4-(2-dimethylaminoethylamino)anthracene-9,10-dione (A)

1-(3-aminopropylamino)-4-methoxyanthracene-9,10-dione

A solution of 1,3-diaminopropane (2.07 g, 28 mmol) and 1,4 dimethoxyanthraquinone (1.50 g, 5.6 mmol) in freshly distilled $CH_2Cl_2$ (1.5 l) was fitted with a reflux condenser, and irradiated with a sunlamp for 6 h. The solvent was distilled and the crude mixture was dried in vacuo overnight. The crude product was triturated with warm petroleum ether to remove excess amine. Chromatography (silica gel $CCl_4$ and $CH_2Cl_2$, 1:1) was performed by slowly increasing the polarity of the solvent to $CH_2Cl_2$ to remove the unreacted 1,4-dimethoxyanthraquinone. Upon elution with methanol, a purple band slowly developed. A purple oil remained upon removal of the solvent. The oil was extracted with warm $CCl_4$, and crystallized by adding petroleum ether to the combined $CCl_4$ extracts. Crystallization afforded a purple solid, 0.48 g (28%) in three crops. Recrystallization from a mixture of $CCl_4$ and petroleum ether afforded an analytical sample: mp 108°–110° C.; $^1H$ NMR $(CDCl_3)\delta 9.95$ (broad t, 1H), 8.21–8.25 (m, 2 H), 7.68–7.73 (m, 2 H), 7.37 (d, 1 H), 7.17 (d, 1H), 4.00(s, 3 H), 3.39–3.48 (m, 2 H), 2.94 (t,2 H), 1.86–1.98 (m, 2 H), 1.36 (broad s, 2H). Anal. Calcd. for $C_{18}H_{18}N_2O_3$: C, 69.66; H, 5.85, N, 9.03. Found: C, 69.75; H 5.95; N, 8.95.

(B)

1-(3-aminopropylamino)-4-(2-dimethylaminoethylamino)anthracene-9,10-dione

A solution of the above 4-methoxydione (0.20 g, 0.55 mmol) and 2-dimethylaminoethylamine (5.0 mL, 57 mmol) was refluxed with stirring for 3 h. The reaction mixture was cooled and poured into a saturated brine solution. The mixture was allowed to stand for 6 h, then filtered. The resulting solid was dried in vacuo, and extracted with $CHCl_3$. The chloroform was removed under reduced pressure to afford a blue solid (0.19 g). Recrystallization from a mixture of $CCl_4$ and petroleum ether gave a blue crystalline solid, 0.13 g (55%) in two crops. A second recrystallization from a mixture of petroleum ether and xylene afforded a sample of mp 111°–113° C.; $^1H$ NMR $(CDCl_3)\delta 10.77$ (broad t, 2 H), 8.31–8.38 (m,2 H), 7.66–7.72 (m, 2H), 7.27 (s, 2 H), 3.47–3.54 (m, 4 H), 2.93 (t, 2 H), 2.68 (t, 2 H), 2.35 (s, 6 H), 1.88(relative 1.97 (m, 2 H), 1.42 (broad s, 2 H); mass spec m/e intensity) 366 (M+3.3), 321 (5.2), 84 (10.8), 58 (100). Analyzed as the acetamide derivative.

EXAMPLE 2

1-(3-acetamidopropylamino)-4-(2-dimethylaminoethylamino)anthracene-9,10-dione (A)

1,3-diaminopropane (4.15 g, 55 mmol) was added to a solution of 1,4-dimethoxyanthraquinone (3.00 g, 11 mmol) in $CH_2Cl_2$ (1.5 L). The flask was fitted with a reflux condenser and the reaction mixture was irradiated with a sunlamp for 7 h. The was dried in vacuo overnight. The residue was dissolved in 100 ml of $CH_2Cl_2$ and absorbed onto silica gel. This was introduced to a column of silica gel and $CH_2Cl_2$. The starting material was eluted with $CH_2Cl_2$. 30 ml of acetic anhydride was then added to the column. The amide was eluted with $CHCl_3$ and collected as two fractions, which upon removal of solvent gave a combined yield, 1.36 g (35%). Recrystallization from xylene afforded purple needles: mp 153°–5° C.: $^1H$ NMR $(CDCl_3)\delta 9.89$ (broad t, 1 H), 8.17–8.23 (m, 2 H), 7.65–7.73 (m, 2 H), 7.26 (d, 1 H), 7.02 (d, 1 H), 6.12 (broad t, 1 H), 3.98 (s, 3 H), 3.43–3.55 (m, 2 H), 3.31–3.40 (m, 2 H), 2.08 (s, 3 H), 1.92–2.08 (m, 2 H); Anal. Calcd. for $C_{20}H_{20}N_2O_4$;

C, 68.17; H, 5.72; N, 7.95. Found: C, 68.35; H, 5.69; N, 7.88.

(B)

1-(3-acetamidopropylamino)-4-(2-dimethylaminoethylamino)anthracene-9,10-dione

The above amide (0.630 g, 2.0 mmol) was refluxed with stirring in 2-dimethylaminoethylamine (6.5 ml) for 5 h. The reaction mixture was poured into saturated sodium chloride solution (75 ml) and allowed to stand overnight. The crude product was filtered, washed with water, and dried in vacuo. The solid obtained was dissolved in $CHCl_3$ and to this solution was added silica gel. The solvent was removed and the silica gel was added to a column (silica gel/$CH_2Cl_2$). Starting material was eluted with $CHCl_3$ and product with $CH_3OH$. The solvent was removed to give a blue solid, 0.510 g (70%). An analytical sample was prepared by recrystallization; mp 193°–194° C.; $^1H$ NMR $(CDCl_3)\delta10.65$–10.78 (m, 2 H), 8.24–8.36 (m, 2 H), 7.62–7.72 (m, 2 h), 7.10–7.20 (m, 2 H), 6.03 (broad t, 1 H), 3.39–3.52 (m, 6 H), 2.68 (t, 2 H), 2.36 (s, 6H), 1.92–2.05 (m, 5 H). Anal. Calcd. for $C_{23}H_{28}N_4O_3$: C, 67.62; H, 6.91; N, 13.72. Found: C, 67.49; H, 6.70; N, 13.73.

EXAMPLE 3

1-(4-acetamidobutylamino)-4-(2-dimethylaminoethylamino)anthracene-9,10-dione

(A)

1-(4-acetamidobutylamino)-4-methoxyanthracene-9,10-dione

Distilled 1,4-diaminobutane (4.9 g, 56 mmol) was added to a solution of 1,4-dimethoxyanthraquinone (3.0 g, 11 mmol) in $CH_2Cl_2$ (1.5 L). This mixture was irradiated for 7 h. The solvent was removed by distillation, the residue was dissolved in methanol (15 mL), and the methanol solution was poured into saturated NaCl (100 mL). On standing overnight, the solid was collected by filtration and then dried. The solid was extracted with warm $CHCl_3$ ( 3×35 mL) and silica gel was added to the combined $CHCl_3$ extracts. The solvents were removed and the silica gel was added to a column and acetylation and chromatography was performed as above. A purple solid was obtained, 1.21 g (30%); mp 151°–153° C.; $^1H$ NMR $(CDCl_3)\delta9.91$ (br t, 1 H), 8.18–8.24 (m, 2 H), 7.66–7.73 (m, 2 H), 7.37 (d, 1 H), 7.11 (d, 1 H), 5.67 (broad t, 1 H), 3.99 (s, 3 H), 3.30–3.42 (m, 4 H), 2.01 (s, 3 H), 1.64–1.86 (m, 4 H). Anal. Calcd. for $C_{21}H_{22}N_2O_4$: C, 68.84; H, 6.05; N,7.65. Found C, 68.57; H, 6.34; N, 7.52.

(B)

1-(4-acetamidobutylamino)-4-(2-dimethylaminoethylamino)anthracene-9,10-dione

The above amide (1.0 g, 2.9 mmol) was refluxed with stirring in 2-dimethylaminoethylamine (10 ml) for 5 h. The reaction mixture was cooled slightly and poured into saturated sodium chloride. The crude product was filtered, washed with water, and dried to yield a blue solid. The solid was chromatographed on silica gel. Starting material was eluted with $CH_2Cl_2$. Product was eluted with 10% $CH_3OH$ in $CHCl_3$ to give a blue solid, 0.91 g (79%). Recrystallization from xylene, then toluene, gave a blue solid: mp 160°–162° C.; $^1H$ NMR $(CDCl_3)\delta10.73$–10.82 (m 2 H), 8.28–8.40 (m, 2 H), 7.65–7.72 (m, 2 H), 5.73 (broad t, 1 H), 3.28–3.55 (m, 6 H), 2.68 (t, 2 H), 2.37 (s, 6 H), 2.01 (s, 3 H), 1.67–1.84 (m, 4H). Anal. Calcd. for $C_{24}H_{30}N_4O_3$: C, 68.22; H, 7.16; N, 13.26. Found: C, 68.13; H, 7.12; N, 13.03.

EXAMPLE 4

1-(4-aminobutylamino)-4-(2-dimethylaminoethylamino)anthracene-9,10-dione

(A)

1-(4-aminobutylamino)-4-methoxyanthracene-9,10-dione 1,4-Diaminobutane (1.65 g, 19 mmol) was added to a solution of 1,4-dimethoxyanthracene-9,10-dione (1.0 g, 3.7 mmol) in $CH_2Cl_2$ (700 ml). After seven, hours of irradiation, the solvent was removed and the residue chromatographed on silica gel. Starting material was eluted with $CHCl_3$ and the product with 5% $CH_3OH$ in $CHCl_3$. A purple solid (0.61 g, 50%) was obtained which was converted to the benzyloxycarbonyl derivative.

(B)

1-(4-benzyloxycarbamoylbutylamino)-4-methoxyanthracene- 9,10-dione

To a stirred solution of 1-(4-aminobutylamino)-4-methoxyanthracene-9,10-dione (0.68 g, 2.1 mmol) and triethylamine (0.23 g. 2.3 mmol) in $CHCl_3$ (30 ml) is added, in one portion, benzylchloroformate (0.393 g, 2.3 mmol). The reaction mixtured is stirred for 1 h. at room temperature. The solvent is removed under reduced pressure and the residue is chromatographed (silica gel, $CHCl_3$). This yields 0.82 g (85%) as a dark purple solid. Recrystallization from toluene gives purple needles melting at 147°–9° C. An analytical sample was prepared by a second crystallization from toluene. $^1H$ NMR $(CDCl_3)\delta9.80$ (br t, 1 H), 8.15 (m, 2 H), 7.62 (m, 2 H), 7.16–7.35 (m, 7 H), 5.19 (br t, 1 H), 5.09 (s, 2 H), 3.90 (s, 3 H), 3.21 (m, 4 H), 1.68 (m, 4 H); MS m/e (relative intensity) 381.2 (100.0), 85.0 (73.0). Anal. Calcd. for $C_{27}H_{26}N_2O_5$: C,70.72; H,5.71; N, 6.10. Found: C, 70.74; H, 5.93; N, 6.01.

(C)

1-(4-benzyloxycarbamoylbutylamino)-4-(2-dimethylaminoethylamino)-anthracene-9,10-dione The above compound (0.28 g, 0.62 mmol) and N,N-dimethylethylenediamine (3 ml) are stirred under reflux for 5 h. The hot reaction mixture is poured into saturated brine. The resultant blue gummy material is collected by filtration and chromatographed (silica gel, 2% $CH_3OH$ in $CHCl_3$) to give 0.17 g (53%) as a blue solid which is crystallized from toluene to give blue needles. Mp 146.5°–8° C.; $^1H$ NMR $(CDCl_3)$ $\delta10.72$ (m, 2 H) 8.31 (m, 2 H), 7.65 (m, 2 H), 7.38–7.24 (m, 5 H), 7.13 (m, 2 H), 5.10 (s, 2 H), 5.06 (brs, 1 H), 3.51–3.19 (m, 6 H), 2.66 (t, 2 H), 2.33 (s, 6 H), 1.81–1.61 (m, 4 H); MS, m/e (relative intensity) 514.2 (27, M+), 58.1 (100). Anal. Calcd. for $C_{30}H_{34}N_4O_4$; C, 70.01; H, 6.65; N, 10.88. Found: C, 70.23; H, 6.63; N, 10.69.

(D)

1-(4-aminobutylamino)-4-(2-dimethylaminoethylamino)anthracene-9,10-dione

Palladium on carbon (10%, 100 mg) is added to a solution of the above carbobenzoxy derivative (0.0500 g), toluene (4 ml), ethanol (4 ml), and cyclohexane (2 ml). The resultant mixture is stirred under reflux for 1 h. The catalyst is filtered from the hot solution. Concentration under vacuum gives 0.0156 g (37%) as an amorphous blue solid; m.p. 88°-90°. $^1$H NMR (CDCl$_3$) δ10.80 (br s, 2 H), 8.35 (m, 2 H), 7.69 (m, 2 H), 7.26 (s, 2 H), 3.48 (m, 4H), 2.80 (br s, 2 H), 2.69 (t, 2 H), 2.36 (s, 6 H), 1.83 (m, 4 H), 1.68 (m, 2 H); CI-MS, m/e (relative intensity) 380 (94, M+), 58 (100). Analyzed as the benzyl carbamate.

This compound showed outstanding antineoplastic activity when tested in vitro. It gave an IP$_{50}$ (1240) of 0.0045 μg/ml which is better than that of any symmetrical compound.

EXAMPLE 5

1-(5-acetamidopentylamino)-4-(2-dimethylaminoethylamino)anthracene-9,10-dione (A)

1-(5-acetamidopentylamino)-4-methoxyanthracene-9,10-dione

A stirred solution of 1,4-dimethoxyanthraquinone (0.54 g, 2 mmol) and 1,5-diaminopentane (0.623 g, 6 mmol) in CH$_2$Cl$_2$ (500 mL) was photolyzed for 48 h. The solvent was removed and the residue chromatographed on silica gel. The unreacted starting material was eluted with 2% methanol in CHCl$_3$. Acetic anhydride (30 mL) is then introduced to the column and the amide is eluted with 4% methanol in CHCl$_3$. Elution of a major magenta band affords 0.303 g (39%). Recrystallization from xylene yields purple needles melting at 145°-147°C.; $^1$H NMR (CDCl$_3$) δ9.88 (broad t, 1 H), 8.21 (m, 2 H), 7.69 (m, 2 H), 7.19 (dd, 2 H), 6.01 (br t, 1 H), 3.97 (s, 3 H), 2.00 (s, 3 H), 1.76 (m, 2 H), 1.56 (m, 4 H), mass spec m/e 380.2 (M+). Anal. Calcd. for C$_{22}$H$_{24}$N$_2$O$_4$: C, 69.46; H, 6.36; N 7.36. Found: C, 69.76, H, 6.57; N, 7.11.

(B)

1-(5-acetamidopentylamino)-4-(2-dimethylaminoethylamino)anthracene-9,10-dione

The above compound (0.20 g, 0.53 mmol) and 2-dimethylaminoethylamine (2 ml) were heated under reflux for 5 h. The cooled reaction mixture was poured into saturated brine (12 ml). The crude product was filtered and washed with water. Chromatography over silica gel eluting with CHCl$_3$, 2% CH$_3$OH in CHCl$_3$, then 5% and finally 10% CH$_3$OH in CHCl$_3$ led to 0.21 g (92%). Recrystallization from toluene gave pure blue needles, mp 138°-139° C.; $^1$H NMR (CDCl$_3$)δ10.80 (broad t, 2 H), 8.35 (m, 2 H), 7.69 (m, 2 H), 7.27 (s, 2 H), 5.63 (s, 1 H), 3.53 (dt, 2 H), 3.43 (dt, 2 H), 3.30 (dt, 2 H), 2.68 (t, 2 H), 2.36 (s, 6 H), 1.97 (s, 3 H), 1.80 (m, 2 H), 1.58 (m, 4 H). mass spec m/e 437 (100%); Anal. Calcd. for C$_{25}$H$_{32}$N$_4$O$_3$; C, 68.78; H, 7.39; N, 12.83. Found: C, 68.83; H, 7.62; N, 12.77.

We claim:

1. A compound having the formula

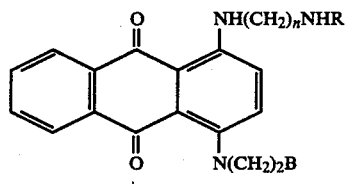

wherein:
B represents a radical selected from a dialkyl amino group having 1 to 4 carbons and a N-heterocyclic radical having 4, 5 or 6 carbon atoms,
n represents 3, 4 or 5, and
R represents alkanoyl or a non-toxic physiologically acceptable salt thereof.

2. A compound according to claim 1, wherein B represents a dialkyl amino group selected from dimethylamino and diethylamino.

3. A compound according to claim 1, wherein B represents a radical selected from the group consisting of morpholino, pyrrolidino and piperidino.

4. A compound according to claim 1, wherein R is selected from the group consisting of acetyl, propionyl and methanesulfonyl.

5. A compound according to claim 1, wherein R is acetyl.

6. A compound according to claim 1, wherein n is 3.

7. A compound according to claim 1, wherein n is 4.

8. A compound according to claim 1, wherein n is 5.

9. A compound according to claim 1, where R represents COCH$_3$, n represents 3, B represents (CH$_3$)$_2$N.

10. A compound according to claim 1, where R represents COCH$_3$, n represents 4, and B represents (CH$_3$)$_2$N.

11. A compound according to claim 1, where R represents COCH$_3$, n represents 5, and B represents (CH$_3$)$_2$N.

* * * * *